(12) United States Patent
Potenziano

(10) Patent No.: US 12,285,008 B2
(45) Date of Patent: *Apr. 29, 2025

(54) METHODS TO IMPROVE ORGAN VIABILITY

(71) Applicant: Mallinckrodt Pharmaceuticals Ireland Limited, Dublin (IE)

(72) Inventor: Jim Potenziano, Hazelwood, MO (US)

(73) Assignee: MALLINCKRODT PHARMACEUTICALS IRELAND LIMITED, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 18/409,181

(22) Filed: Jan. 10, 2024

(65) Prior Publication Data
US 2024/0138399 A1 May 2, 2024

Related U.S. Application Data

(63) Continuation of application No. 17/360,916, filed on Jun. 28, 2021, now Pat. No. 11,950,590, which is a continuation of application No. 16/112,297, filed on Aug. 24, 2018, now Pat. No. 11,044,904.

(60) Provisional application No. 62/550,463, filed on Aug. 25, 2017.

(51) Int. Cl.
*A01N 1/02* (2006.01)
*A61B 17/00* (2006.01)

(52) U.S. Cl.
CPC .......... *A01N 1/021* (2013.01); *A01N 1/0226* (2013.01); *A01N 1/0247* (2013.01); *A61B 17/00* (2013.01); *A61B 2017/00969* (2013.01)

(58) Field of Classification Search
None
See application file for complete search history.

(56) References Cited

U.S. PATENT DOCUMENTS

| 5,494,822 | A | 2/1996 | Sadri |
| 7,238,469 | B2 | 7/2007 | Bach et al. |
| 7,410,474 | B1 | 8/2008 | Friend et al. |
| 8,084,195 | B2 | 12/2011 | Young |
| 9,629,358 | B2 | 4/2017 | Potenziano et al. |
| 9,706,769 | B2 | 7/2017 | Taylor et al. |
| 11,044,904 | B2 * | 6/2021 | Potenziano ............ A61B 17/00 |
| 11,950,590 | B2 * | 4/2024 | Potenziano .......... A01N 1/0247 |
| 2017/0215411 | A1 | 8/2017 | Potenziano et al. |

FOREIGN PATENT DOCUMENTS

| JP | 2005500875 A | 1/2005 |
| JP | 2010530001 A | 9/2010 |
| JP | 2015110642 A | 6/2015 |
| JP | 2017503762 A | 2/2017 |
| JP | 2017061513 A | 3/2017 |
| JP | 2020511359 A | 4/2020 |
| WO | 0165935 A1 | 9/2001 |
| WO | 03000114 A2 | 1/2003 |
| WO | 2008157393 A1 | 12/2008 |
| WO | 2015084698 A2 | 6/2015 |
| WO | 2017100730 A1 | 6/2017 |

OTHER PUBLICATIONS

Dong B.M., et al., "Nitric Oxide Ventilation of Rat Lungs from Non-Heart-Beating Donors Improves Post transplant Function," American Journal of Transplantation, Nov. 2009, vol. 9, pp. 2707-2715.
Extended European Search Report issued in European Application No. EP18848433.1, mailed on Apr. 21, 2021, 11 Pages.
Fujiwara H., et al., "NO Inhalation Therapy (at National Children's Hospital), The Japanese Journal of Respiratory Care, 1995, vol. 12(1), pp. 37-45.
International Preliminary Report on Patentability for International Application No. PCT/US2018/048028, mailed on Mar. 5, 2020, 7 Pages.
International Search Report and Written Opinion for International Application No. PCT/US2018/048028, mailed Oct. 10, 2018, 10 Pages.
Kyota F., et al., "Role of Nitric Oxide in Liver Transplantation: Should it be Routinely Used?," World Journal of Hepatology, vol. 8 (34), Jan. 1, 2016, pp. 1489-1496, XP055775762.
Namihira T., et al., "Development of NO Generator for Medical Applications", IEEJ Transactions on Electronics Information and Systems, vol. 124(1), Apr. 2004, pp. 215-216.
Office Action for Australian Application No. 2018322317, mailed on Jun. 14, 2023, 3 pages.
Office Action for Canadian Application No. 3,073,399 mailed on Sep. 1, 2023, 4 pages.
Office Action for Chinese Patent Application No. 201880059363.9, mailed May 25, 2022, 16 Pages.
Office Action for European Patent Application No. 18848433.1, mailed Dec. 15, 2021, 8 Pages.
Office Action for Japanese Application No. 2022-123251, mailed on Nov. 2, 2023, 7 pages.
Office Action for Japanese Patent Application No. 2020511359, mailed Nov. 4, 2022, 5 Pages.
Office Action for Japanese Patent Application No. 2020511359, mailed May 6, 2022, 14 Pages.
Office Action for Korean Application No. 10-2020-7007478, mailed on Nov. 29, 2023, 5 pages.
Office Action for U.S. Appl. No. 17/360,916, mailed on May 25, 2023, 14 pages.
Shimamura T., et al., "Protective Role of Nitric Oxide in Ischemia and Reperfusion Injury of the Liver," Journal of American College of Surgeons, Jan. 1, 1999, vol. 188 (1), pp. 43-52, XP055775763.
Office Action for Mexican Application No. MX/a/2020/001853, mailed on Apr. 5, 2024, 8 pages.

(Continued)

*Primary Examiner* — Blaine Lankford

(57) ABSTRACT

The present disclosure provides methods to improve the viability of an organ, or organs, by continuously administering a composition comprising $NO_x$ gas directly to the organ(s).

27 Claims, 2 Drawing Sheets

(56) References Cited

OTHER PUBLICATIONS

Fukazawa, et al., Role of nitric oxide in liver transplantation: should it be routinely used? World Journal of Hepatology, 8(34), published Jan. 1, 2016, pp. 1489-1496.

* cited by examiner

METHODS TO IMPROVE ORGAN VIABILITY

CROSS REFERENCE TO RELATED APPLICATIONS

This application is a continuation application of U.S. application Ser. No. 17/360,916, filed Jun. 8, 2021, which is a continuation application of U.S. application Ser. No. 16/112,297, filed Aug. 24, 2018, now patented as U.S. Pat. No. 11,044,904 which claims priority to U.S. provisional application No. 62/550,463, filed Aug. 25, 2017, the disclosures of which are hereby incorporated by reference in their entirety.

FIELD

The present disclosure provides methods to improve the viability of an organ, or organs, by continuously administering a composition comprising $NO_x$ gas directly to the organ(s).

BACKGROUND

Cells, tissues, organs, and organisms that are deprived of appropriate blood flow undergo ischemic damage due to oxidative stress and eventually die. Traditional methods of reducing ischemic damage involve perfusing affected tissues with oxygen, but this procedure can cause significant tissue damage and can result in serious and/or permanent injury, such as brain damage during stroke or cardiac arrest.

Attempts have been made to reduce ischemia and reperfusion injury by inducing tissues and organs to enter a reduced metabolic state. For example, in the context of living tissues being preserved for transplant or grafting, one common method for reducing their metabolic activity is by immersing tissues or organs in a physiologic fluid, such as saline, and placing them in a cold environment. However, such methods cannot be relied upon for extended periods, and the success of organ transplant and limb reattachments remains inversely related to the time the organ or limb is out of contact with the intact organism.

Thus, there remains a need in the art for organs with improved viability prior ischemia and/or reperfusion injury.

SUMMARY

In an aspect, the present disclosure encompasses a method to improve the viability of an organ intended for transplant, the method comprising continuously administering a composition comprising $NO_x$ gas directly to the organ via an organ perfusion system or ventilation.

In another aspect, the present disclosure encompasses a method to improve the viability of an organ damaged by ischemia-reperfusion, the method comprising continuously administering a composition comprising not more than about 20 ppm of $NO_x$ gas directly to the organ via an organ perfusion system or ventilation. In various embodiments, the organ in need of treatment is an organ that sustained damage due to traumatic injury, surgery, respiratory arrest, or cardiac arrest. In certain embodiments, the organ in need of treatment is an organ intended for transplant. In exemplary embodiments, the organ in need of treatment is an organ intended for transplant that has been removed from a donor.

In another aspect, the present disclosure encompasses a method to improve the viability of an organ damaged by ischemia-reperfusion, the method comprising (a) administering to the organ a composition comprising about 20 ppm to about 40 ppm $NO_x$ gas ("a loading dose") for up to about 1 hour ("a loading period"), and then (b) continuously administering a composition comprising not more than about 20 ppm of $NO_x$ gas directly to the organ via an organ perfusion system or ventilation. In various embodiments, the organ in need of treatment is an organ that sustained damage due to traumatic injury, surgery, respiratory arrest, or cardiac arrest. In certain embodiments, the organ in need of treatment is an organ intended for transplant. In exemplary embodiments, the organ in need of treatment is an organ intended for transplant that has been removed from a donor.

In another aspect, the present disclosure encompasses a method to improve the viability of an organ intended for transplant, the method comprising continuously administering a composition comprising 20 ppm or less of $NO_x$ gas directly to the organ via an organ perfusion system or ventilation. In some embodiments the organ resides in a brain dead donor. In other embodiments, the organ has been removed from a donor prior to administration of the composition comprising the $NO_x$ gas. In exemplary embodiments, the organ is a lung, a kidney, or a heart.

In another aspect, the present disclosure encompasses a method to improve the viability of an organ intended for transplant, the method comprising (a) administering to the organ a composition comprising about 20 ppm to about 40 ppm $NO_x$ gas ("a loading dose") for up to about 1 hour ("a loading period"), and then (b) continuously administering a composition comprising 20 ppm or less of $NO_x$ gas directly to the organ via an organ perfusion system or ventilation. In some embodiments the organ resides in a brain dead donor. In other embodiments, the organ has been removed from a donor prior to administration of the composition comprising the $NO_x$ gas. In exemplary embodiments, the organ is a lung, a kidney, or a heart.

In another aspect, the present disclosure encompasses methods to treat ischemia-reperfusion damage in an organ in need thereof, the method comprising continuously administering a composition comprising 20 ppm or less of $NO_x$ gas directly to the organ via an organ perfusion system or ventilation. In various embodiments, the organ in need of treatment is an organ that sustained damage due to traumatic injury, surgery, respiratory arrest, or cardiac arrest. In certain embodiments, the organ in need of treatment is an organ intended for transplant. In exemplary embodiments, the organ in need of treatment is an organ intended for transplant that has been removed from a donor.

In another aspect, the present disclosure encompasses methods to treat ischemia-reperfusion damage in an organ in need thereof, the method comprising (a) administering to the organ a composition comprising about 20 ppm to about 40 ppm $NO_x$ gas ("a loading dose") for up to about 1 hour ("a loading period"), and then (b) continuously administering a composition comprising 20 ppm or less of $NO_x$ gas directly to the organ via an organ perfusion system or ventilation. In various embodiments, the organ in need of treatment is an organ that sustained damage due to traumatic injury, surgery, respiratory arrest, or cardiac arrest. In certain embodiments, the organ in need of treatment is an organ intended for transplant. In exemplary embodiments, the organ in need of treatment is an organ intended for transplant that has been removed from a donor.

In another aspect, the present disclosure provides methods for transplantation, the method comprising (a) continuously administering a composition comprising 20 ppm or less of $NO_x$ gas directly to an organ intended for transplant for up to 12 hours, and (b) transplanting the organ into a recipient.

In some embodiments the organ resides in a brain dead donor. In other embodiments, the organ has been removed from a donor prior to administration of the composition comprising the $NO_x$ gas. In exemplary embodiments, the organ is a lung, a kidney, or a heart.

In another aspect, the present disclosure provides methods for transplantation, the method comprising (a) administering to the organ a composition comprising about 20 ppm to about 40 ppm $NO_x$ gas ("a loading dose") for up to about 1 hour ("a loading period"), then (b) continuously administering a composition comprising 20 ppm or less of $NO_x$ gas directly to an organ intended for transplant for up to 12 hours, and then (c) transplanting the organ into a recipient. In some embodiments the organ resides in a brain dead donor. In other embodiments, the organ has been removed from a donor prior to administration of the composition comprising the $NO_x$ gas. In exemplary embodiments, the organ is a lung, a kidney, or a heart.

Other aspects and iterations of the disclosure are described more thoroughly below.

DETAILED DESCRIPTION

Figure 1:
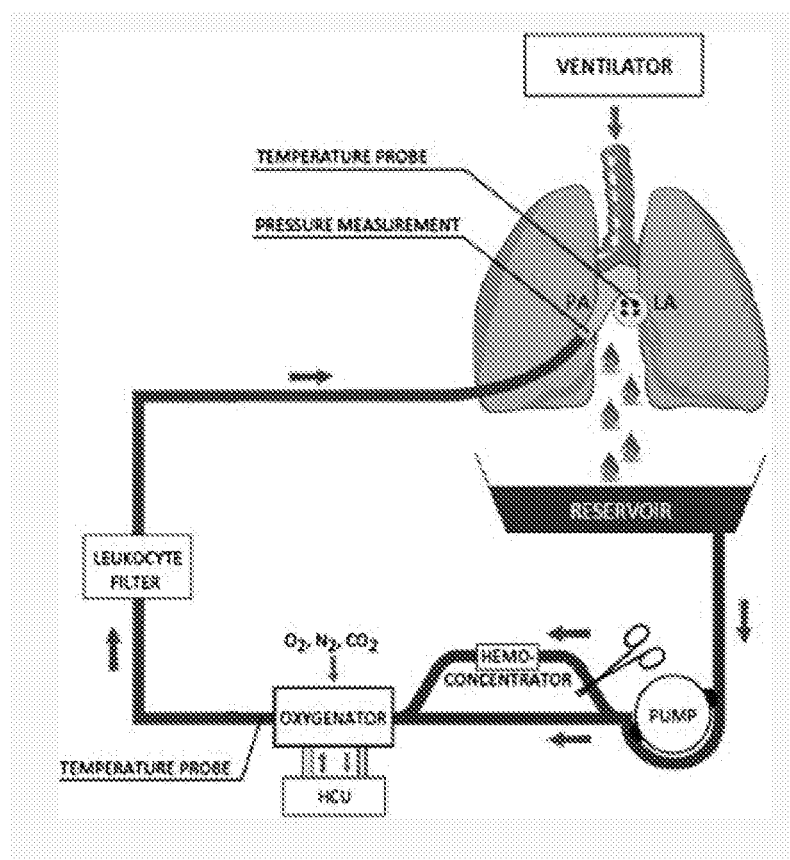
FIG. 1 is an illustration of an embodiment of an EVLP circuit.

The present disclosure provides methods to improve the viability of an organ, or organs, by continuously administering a composition comprising $NO_x$ gas directly to the organ(s). The disclosure encompasses methods to improve the viability of organs intended for transplant, as well as organs with ischemia-reperfusion damage from other causes. Also provided by the present disclosure are methods to improve the performance of transplanted organs and methods for transplantation. As used herein the term "$NO_x$ gas" refers to gaseous nitrogen oxides. In preferred embodiments, the $NO_x$ gas is gaseous nitric oxide (gNO). Non-limiting examples of further components of the composition may include an inert diluent gas (e.g. helium, neon, etc.), human albumin, sodium caprylate, N-acetyl-DL-tryptophan, and oxygen gas ($O_2$). Continuously administering a composition comprising $NO_x$ gas directly to an organ means the organ will be in direct contact with the $NO_x$ gas without interruption for the duration of the administration. The present disclosure is not limited by type of organ. Non-limiting examples of suitable organs include liver, kidney, pancreas, heart, lung, intestine, thymus, cornea, vascularized composite allografts (e.g. face, hand, etc.), or any combination thereof. The viability of the organ will be improved compared to an organ obtained by a method that did not continuously administer a composition comprising $NO_x$ gas directly to the organ. As used herein, the term "viability" refers to the suitability of an organ for its intended purpose. Measures of an organ's viability may vary depending upon the type of organ, and are known in the art.

Several definitions that apply throughout this disclosure will now be presented. As used herein, "about" refers to numeric values, including whole numbers, fractions, percentages, etc., whether or not explicitly indicated. The term "about" generally refers to a range of numerical values, for instance, 0.5-1%, +1-5% or ±5-10% of the recited value, that one would consider equivalent to the recited value, for example, having the same function or result.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

As used herein, the term "ishcemia-reperfusion damage" refers to damage that occurs due to ischemia, reperfusion, or both.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

(a) Composition Comprising $NO_x$ Gas

According to the present disclosure, a composition comprising $NO_x$ gas is continuously administered directly to an organ. Compositions of the present disclosure may be a gas or a liquid. When compositions of the present disclosure are liquids, the $NO_x$ gas is solubilized in the liquid. Stated another way, a "composition comprising $NO_x$ gas, wherein the composition is a liquid" is a liquid comprising solubilized $NO_x$ gas. Similarly, "a composition comprising 20 ppm $NO_x$ gas, wherein the composition is a liquid" is a liquid comprising 20 ppm of nitric oxide, wherein the 20 ppm nitric oxide is the amount of $NO_x$ gas that is solubilized in the liquid. Moreover, in embodiments where the composition is a liquid, the amount of $NO_x$ gas directly administered to an organ is the amount of $NO_x$ gas solubilized in the liquid. The $NO_x$ gas may be produced and provided by any method known in the art.

In some embodiments, the composition is a gas. In addition to the $NO_x$ gas, the composition may further comprise one or more additional components including, but not limited to, inert diluent gas(es) (e.g., helium, neon, etc.), nitrogen, oxygen, and water. In an exemplary embodiment, the $NO_x$ gas is gNO. When the composition is a gas, the composition may be directly administered to an organ via a ventilator or any other method known in the art.

In other embodiments, the composition is a perfusion fluid. The term "perfusion fluid" refers to any fluid used in the preservation, perfusion, or reperfusion of tissues or organs. Perfusion fluids are often sterile and isotonic. In addition to the solubilized $NO_x$ gas, the perfusion fluid may further comprise one or more additional components including, but not limited to sodium caprylate, N-acetyl-DL-tryptophan, and human albumin. The composition of the perfusion fluid may also vary between organs. In a preferred embodiment, the perfusion fluid is an acellular perfusion fluid. Such solutions may include but are not limited to Celsior solution, Krebs-Henseleit solution, normal saline solution, University of Wisconsin solution, St. Thomas II solution, Collins solution, Stanford solution, Perfidex®, Steen Solution™, or combinations thereof. In an exemplary embodiment, the composition is an acellular perfusion fluid and the $NO_x$ gas is gNO. In further embodiments, the acellular perfusion solution is Steen Solution™, optionally comprising sodium caprylate, N-acetyl-DL-tryptophan, and human albumin. Suitable methods for administering a perfusion solution directly to an organ are known in the art including, but not limited to, an organ perfusion system. The present disclosure is not limited to any particular organ perfusion system. Generally speaking, an organ perfusion system may comprise a pump for perfusate movement and control, means to control the system temperature, cannulae, and means to measure physiological parameters. A non-limiting example of an organ perfusion system is disclosed in U.S. Pat. No. 9,629,358, incorporated herein by reference. Non-limiting examples of an organ perfusion system are also disclosed in FIG. 1 and FIG. 2.

To improve the viability of an organ, a therapeutically effective amount of $NO_x$ gas is directly administered to an organ. Depending upon the type, or types, of compositions administered, administration of the $NO_x$ gas directly to the organ may occur via an organ perfusion system, a ventilator, or any combination thereof. In embodiments where an organ perfusion system and a ventilator are used in combination, an organ perfusion system and a ventilator may be used simultaneously to administer a composition comprising $NO_x$ gas directly to the organ. Alternatively, or in addition, an organ perfusion system and a ventilator may be used sequentially to administer a composition comprising $NO_x$ gas directly to the organ, including various amounts of overlap between the two methods of administration (e.g. no overlap, or an overlap of a few seconds, minutes, or hours). For example, administration may occur first with a ventilator and then a perfusion system, or vice versa.

A "therapeutically effective amount of $NO_x$ gas" refers to an amount of $NO_x$ gas that, when directly administered to an organ, is sufficient to improve the viability of the organ as defined herein. The amount of $NO_x$ which constitutes a "therapeutically effective amount" will vary depending on a variety of factors, but may be determined by one of ordinary skill in the art. As further detailed below, a therapeutically effective amount of $NO_x$ gas for the treatment of organs with ischemia-reperfusion damage is 20 ppm or less. This therapeutically effective amount of $NO_x$ gas may be used alone or after administration of a loading dose of $NO_x$ gas. A loading dose of $NO_x$ gas may be used to increase vasodilation of an ischemic organ, and may be particularly suitable when compositions of the present disclosure are first contacted with an organ after it has been removed a donor. However, the amount of $NO_x$ gas provided in a loading dose typically exceeds the amount of $NO_x$ gas that can be used to safely treat ischemia-reperfusion damage for an extended period of time (e.g. periods of time greater than one hour).

In one or more embodiments, the $NO_x$ gas is administered at an initial concentration, and optionally increased as necessary to obtain the desired effect (e.g., increased viability of the organ). For example, the initial nitric oxide concentration may be about 0.05 ppm to about 50 ppm or about 1 ppm to about 50 ppm and optionally increased incrementally until the desired effect is obtained or a nitric oxide threshold is met. An exemplary nitric oxide administration may begin at an initial concentration of about 1 ppm, then increased in increments of about 0.1 ppm to about 5 ppm until the desired $NO_x$ effect is obtained, but ensuring that the $NO_x$ concentration does not exceed 50 ppm and/or that the methemoglobin levels do not meet or exceed about 5%. Alternatively, an exemplary nitric oxide administration may begin at an initial concentration of 5 ppm, then increased in increments of 0.1 ppm to 5 ppm until the desired $NO_x$ effect is obtained, but ensuring that the $NO_x$ concentration does not exceed 50 ppm and/or that the methemoglobin levels do not meet or exceed about 5%. In another exemplary embodiment, nitric oxide administration may begin at an initial concentration of 10 ppm, then increased in increments of 0.1 ppm to 5 ppm until the desired $NO_x$ effect is obtained, but ensuring that the $NO_x$ concentration does not exceed 50 ppm and/or that the methemoglobin levels do not meet or exceed about 5%. In still another exemplary embodiment, nitric oxide administration may begin at an initial concentration of 15 ppm, then increased in increments of 0.1 ppm to 5 ppm until the desired $NO_x$ effect is obtained, but ensuring that the $NO_x$ concentration does not exceed 50 ppm and/or that the methemoglobin levels do not meet or exceed about 5%. In yet another exemplary embodiment, nitric oxide administration may begin at an initial concentration of 20 ppm, then increased in increments of 0.1 ppm to 5 ppm until the desired $NO_x$ effect is obtained, but ensuring that the $NO_x$ concentration does not exceed 50 ppm and/or that the methemoglobin levels do not meet or exceed about 5%. In each of the above embodiments, administration may be for 5, 10, 15, 30 or 60 min. Alternatively, administration may be for 1, 2, 3, 4, 5, 6, 7, 8, 9, 10, 11, or 12 hours.

In one or more embodiments, the $NO_x$ gas is administered at an initial concentration, and optionally increased as necessary to obtain the desired effect (e.g., increased viability of the organ). For example, the initial nitric oxide concentration may be about 0.05 ppm to about 35 ppm or about 1 ppm to about 35 ppm and optionally increased incrementally until the desired effect is obtained or a nitric oxide threshold is met. An exemplary nitric oxide administration may begin at an initial concentration of about 1 ppm, then increased in increments of about 0.1 ppm to about 5 ppm until the desired $NO_x$ effect is obtained, but ensuring that the $NO_x$ concentration does not exceed 35 ppm and/or that the methemoglobin levels do not meet or exceed about 5%. Alternatively, an exemplary nitric oxide administration may begin at an initial concentration of 5 ppm, then increased in increments of 0.1 ppm to 5 ppm until the desired $NO_x$ effect is obtained, but ensuring that the $NO_x$ concentration does not exceed 35 ppm and/or that the methemoglobin levels do not meet or exceed about 5%. In another exemplary embodiment, nitric oxide administration may begin at an initial concentration of 10 ppm, then increased in increments of 0.1 ppm to 5 ppm until the desired $NO_x$ effect is obtained, but ensuring that the $NO_x$ concentration does not exceed 35 ppm and/or that the methemoglobin levels do not meet or exceed about 5%. In still another exemplary embodiment, nitric oxide administration may begin at an initial concentration of 15 ppm, then increased in increments of 0.1 ppm to 5 ppm until the desired $NO_x$ effect is obtained, but ensuring that the $NO_x$ concentration does not exceed 35 ppm and/or that the methemoglobin levels do not meet or exceed about 5%. In yet another exemplary embodiment, nitric oxide administration may begin at an initial concentration of 20 ppm, then increased in increments of 0.1 ppm to 5 ppm until the desired $NO_x$ effect is obtained, but ensuring that the $NO_x$ concentration does not exceed 35 ppm and/or that the methemoglobin levels do not meet or exceed about 5%. In each of the above embodiments, administration may be for 5, 10, 15, 30 or 60 min. Alternatively, administration may be for 1, 2, 3, 4, 5, 6, 7, 8, 9, 10, 11, or 12 hours.

In one or more embodiments, the $NO_x$ gas is administered at an initial concentration, and optionally increased as necessary to obtain the desired effect (e.g., increased viability of the organ). For example, the initial nitric oxide concentration may be about 0.05 ppm to about 20 ppm or about 1 ppm to about 20 ppm and optionally increased incrementally until the desired effect is obtained or a nitric oxide threshold is met. An exemplary nitric oxide administration may begin at an initial concentration of about 1 ppm, then increased in increments of about 0.1 ppm to about 5 ppm until the desired $NO_x$ effect is obtained, but ensuring that the $NO_x$ concentration does not exceed 20 ppm and/or that the methemoglobin levels do not meet or exceed about 5%. Alternatively, an exemplary nitric oxide administration may begin at an initial concentration of 5 ppm, then increased in increments of 0.1 ppm to 5 ppm until the desired $NO_x$ effect is obtained, but ensuring that the $NO_x$ concentration does not exceed 20 ppm and/or that the methemoglobin levels do not meet or exceed about 5%. In another exemplary embodiment, nitric oxide administration may begin at an initial concentration of 10 ppm, then increased in increments of 0.1 ppm to 5 ppm until the desired $NO_x$ effect is obtained, but ensuring that the $NO_x$ concentration does not exceed 35 ppm and/or that the methemoglobin levels do not meet or exceed about 5%. In still another exemplary embodiment, nitric oxide administration may begin at an initial concentration of 15 ppm, then increased in increments of 0.1 ppm to 5 ppm until the desired $NO_x$ effect is obtained, but ensuring that the $NO_x$ concentration does not exceed 20 ppm and/or that the methemoglobin levels do not meet or exceed about 5%. In yet another exemplary embodiment, nitric oxide administration may begin at an initial concentration of 20 ppm, then increased in increments of 0.1 ppm to 5 ppm until the desired $NO_x$ effect is obtained, but ensuring that the $NO_x$ concentration does not exceed 20 ppm and/or that the methemoglobin levels do not meet or exceed about 5%. In each of the above embodiments, administration may be for 5, 10, 15, 30 or 60 min. Alternatively, administration may be for 1, 2, 3, 4, 5, 6, 7, 8, 9, 10, 11, or 12 hours.

In one or more embodiments, $NO_x$ gas is administered at an initial concentration for an initial amount of time, and then administered at a second, lower concentration for a second amount of time to obtain the desired effect (e.g., increased viability of the organ). For example, the $NO_x$ gas may be administered at an initial concentration of about 20 ppm to about 40 ppm for up to about 1 hour, and then decreased to 20 ppm or less to improve organ viability. An exemplary nitric oxide administration may begin at an initial concentration of about 20 ppm to about 40 ppm, and then be decreased in increments over the initial amount of time until the nitric oxide concentration is 20 ppm or lower. The rate of decrease may or may not be constant. The nitric oxide concentration may be further adjusted as needed, for example, based on the monitoring of a nitric oxide marker. Alternatively, an exemplary nitric oxide administration may begin at an initial concentration of about 20 ppm to about 40 ppm, held constant for the initial amount of time, and then decreased to a nitric oxide concentration of 20 ppm or less. The nitric oxide concentration may be further adjusted as needed, for example, based on the monitoring of a nitric oxide marker. In each of the above embodiments, the total time of nitric oxide administration (time at initial concentration plus time at decreased concentration) may be 1, 2, 3, 4, 5, 6, 7, 8, 9, 10, 11, or 12 hours.

In each of the above embodiments, the initial nitric oxide concentration, increments of nitric oxide increase or decrease, maximum nitric oxide concentration and/or threshold for the nitric oxide or nitric oxide marker may be varied depending on the application and/or based on the particular organ being treated. The increments may vary throughout the adjustment of the nitric oxide delivery. The nitric oxide may also be incrementally decreased if the monitoring indicates that the nitric oxide or nitric oxide marker meets or exceeds the nitric oxide threshold.

In each of the above embodiments, the $NO_x$ concentration may also be incrementally adjusted by a certain percentage relative to the last $NO_x$ concentration. Such incremental percentages can include 5%, 10%, 15%, 20%, 25%, 30%, 35%, 40%, 45%, 50%, 55%, 60%, 65%, 70%, 75%, 80%, 85%, 90%, 95%, 100%, 110%, 125%, 150%, 175% and 200% changes in the $NO_x$ concentration.

Instead of or in addition to adjusting the $NO_x$ concentration, the $NO_x$ gas administration may be adjusted by any means for adjusting the amount of $NO_x$ gas that is directly delivered to the organ, such as by adjusting the flow rate of the $NO_x$ gas.

In further embodiments, the nitric oxide administration is adjusted based on the monitoring of nitric oxide or a nitric oxide marker. As used herein, "nitric oxide marker" refers to a direct or indirect indicator of nitric oxide concentration in a fluid. For example, nitric oxide markers include, among others, methemoglobin and $NO_x$ (i.e. NO, nitrite ions ($NO_2^-$), nitrate ions ($NO_3^-$), etc.). Such adjustment may be manual or automatically implemented by the $NO_x$ delivery device. The NO delivery device may also provide an alarm based on the monitoring. If the monitoring device is a separate component from the NO delivery device, the monitoring device may transmit the monitoring information to the NO delivery device via any appropriate wired or wireless connection. For example, if the nitric oxide or nitric oxide marker in the fluid is below a certain threshold, NO delivery may be increased until the nitric oxide or nitric oxide marker in the fluid meets the threshold. Similarly, if the nitric oxide or nitric oxide marker in the fluid is above a certain threshold, the amount of NO administered may be decreased. The nitric oxide or nitric oxide marker may be monitored either continuously or intermittently, such as at regular intervals.

In one or more embodiments, such monitoring may comprise monitoring the methemoglobin and/or NO. These nitric oxide markers may be measured directly through techniques such as pulse oximetry or optical measurement or any other means for measuring or co-relating NO or NO markers either directly or indirectly. For example, another measurement technique involves placing a probe in perfusion fluid to measure fluid $NO_x$ levels and may provide real-time analysis of the perfusion fluid.

In one or more embodiments, the nitric oxide or nitric oxide marker is monitored by comparing a measurement of the nitric oxide or nitric oxide marker to a nitric oxide threshold. The nitric oxide threshold may be a safety limitation that ensures that methemoglobinemia does not develop. For example, the nitric oxide threshold may be a methemoglobin level, such as a percentage of methemoglobin relative to the red blood cells. In exemplary embodiments, the nitric oxide threshold is in the range from about 1% to about 15% methemoglobin, or about 3% to about 10% methemoglobin. Accordingly, the nitric oxide administration may be adjusted if the methemoglobin levels meet or exceed an acceptable range, such as ≤3%, ≤4%, ≤5%, 6%, ≤7%, ≤8%, ≤9%, ≤10%, ≤11% or ≤12%.

The level of $NO_2$ may also be monitored in the perfusion fluid. $NO_2$ may build up in the fluids due to recirculation of the fluids. If the $NO_2$ concentration rises above a certain threshold, NO delivery device may adjust the NO administration and/or provide an alarm. The $NO_2$ may also be removed through the use of a reducing agent, scrubber, base, or other appropriate means.

(b) Ischemia-Reperfusion Damage

The term "ischemia-reperfusion damage" refers to damage that occurs due to ischemia, reperfusion, or both. Ischemia refers to an inadequate blood supply to an organ, and ischemic damage occurs when the blood supply to an area of tissue or organ is cut off. The act of restoring the flow of blood to an organ or tissue is referred to as reperfusion, and reperfusion damage occurs as a consequence of restoring blood flow to the tissue or organ after ischemia. Ischemia may be the result of an injury or disease suffered by an organism. Examples of specific diseases that can induce ischemia or hypoxia include, but are not limited to, traumatic injury or surgery, respiratory or cardiac arrest, tumors, heart diseases, and neurological diseases. Examples of specific injuries that can result in ischemic or hypoxic conditions include, but are not limited to, external insults, such as burns, cutting wounds, amputations, gunshot wounds, or surgical trauma. In addition, injuries can also include internal insults, such as stroke or heart attack, which result in the acute reduction in circulation. Other injuries include reductions in circulation due to non-invasive stress, such as exposure to cold or radiation, or a planned reduction in circulation, e.g., during heart surgery, or in the treatment of organ donors prior to removal of donor organs for transport and transplantation into a recipient.

One aspect of the present disclosure encompasses methods to treat ischemia-reperfusion damage in an organ in need thereof. The method comprises continuously administering a composition comprising 20 ppm or less of $NO_x$ gas directly to the organ. In some embodiments, the composition comprises 1 ppm to 20 ppm nitric oxide. In other embodiments, the composition comprises about 1 ppm to about 10 ppm nitric oxide, about 5 ppm to about 15 ppm nitric oxide, or about 10 ppm to 20 ppm. In other embodiments, the composition comprises about 1 ppm, about 2 ppm, about 3 ppm, about 4 ppm, about 5 ppm, about 6 ppm, about 7 ppm, about 8 ppm, about 9 ppm, about 10 ppm, about 11 ppm, about 12 ppm, about 13 ppm, about 14 ppm, about 15 ppm, about 16 ppm, about 17 ppm, about 18 ppm, about 19 ppm, or about 20 ppm nitric oxide. Suitable compositions comprising $NO_x$ gas are described in Section (a). In preferred embodiments, the composition is a perfusion fluid, even more preferably an acellular perfusion fluid. In further embodiments, the acellular perfusion solution is Steen Solution™, optionally comprising sodium caprylate, N-acetyl-DL-tryptophan, and human albumin. In various embodiments, the organ in need of treatment is an organ that sustained damage due to traumatic injury, surgery, respiratory arrest, or cardiac arrest. In certain embodiments, the organ in need of treatment is an organ intended for transplant. In exemplary embodiments, the organ in need of treatment is an organ intended for transplant that has been removed from a donor.

Administration may be for 5, 10, 15, 30 or 60 minutes. Alternatively, administration may be for 1, 2, 3, 4, 5, 6, 7, 8, 9, 10, 11, 12, or more hours. In embodiments where the organ is intended for transplant, administration of the $NO_x$ gas preferably does not exceed a total of 12 hours. In certain embodiments, administration begins at the same time as the ischemia. In other embodiments, administration begins sometime after the ischemia begins, but preferentially as close in time to the start of the ischemia as possible. For example, administration may begin about 5, 10, 15, 20, 25, or 30 min after the start of ischemia. Administration may also start during reperfusion, or alternatively, continue after reperfusion begins. In some instances, administration may continue for 1, 2, 3, 4, 5, 6, 7, 8, 9, 10, 11, 12, or more than 12 hours after reperfusion has begun.

Effective treatment of ischemia-reperfusion damage may be evaluated by any method known in the art, including but not limited to measures of cellular function (e.g., metabolic capacity, ATP content, etc.), measures of cellular damage (e.g. histological assessment, protein oxidation, morphological changes, etc.), measures of inflammation, and/or measures of the organ's function.

In further embodiments, a method to treat ischemia-reperfusion damage in an organ in need thereof may comprise an additional step, wherein a composition comprising about 20 ppm to about 40 ppm $NO_x$ gas ("a loading dose") is administered for up to about 1 hour ("a loading period"), immediately prior to administration of the composition comprising 20 ppm or less of $NO_x$ gas. For example, the loading dose may be administered for about 10 minutes, about 15 minutes, about 20 minutes, about 30 minutes, or for about 10 minutes to about 30 minutes. In another example, the loading dose may be administered for about 30 minutes, about 35 minutes, about 40 minutes, about 40 minutes, about 45 minutes, about 50 minutes, about 55 minutes, about 60 minutes, or for 30 minutes to 60 minutes. With the exception of the nitric oxide concentration, the two compositions may be the same. Alternatively, the two compositions may be different. The concentration of nitric oxide in the loading dose may be decreased in increments over the loading period until the nitric oxide concentration is 20 ppm or lower. The rate of decrease may or may not be constant. Alternatively, the concentration of nitric oxide in the loading dose may be held constant over the loading period, and then decreased to a nitric oxide concentration of 20 ppm or less. In preferred embodiments, the two compositions are the same, and the compositions are a perfusion fluid, preferably an acellular perfusion fluid. In exemplary embodiments, the organ is a heart, a lung, or a kidney, and the organ is intended for transplant.

Another aspect of the disclosure encompasses methods to improve the viability of an organ damaged by ischemia-reperfusion. The method comprises continuously administering a composition comprising 20 ppm or less of $NO_x$ gas directly to the organ. In some embodiments, the composition comprises 1 ppm to 20 ppm nitric oxide. In other embodiments, the composition comprises about 1 ppm to about 10 ppm nitric oxide, about 5 ppm to about 15 ppm nitric oxide, or about 10 ppm to 20 ppm. In other embodiments, the composition comprises about 1 ppm, about 2 ppm, about 3 ppm, about 4 ppm, about 5 ppm, about 6 ppm, about 7 ppm, about 8 ppm, about 9 ppm, about 10 ppm, about 11 ppm, about 12 ppm, about 13 ppm, about 14 ppm, about 15 ppm, about 16 ppm, about 17 ppm, about 18 ppm, about 19 ppm, or about 20 ppm nitric oxide. Suitable compositions comprising $NO_x$ gas are described in Section (a). In preferred embodiments, the composition is a perfusion fluid, even more preferably an acellular perfusion fluid. In further embodiments, the acellular perfusion solution is Steen Solution™, optionally comprising sodium caprylate, N-acetyl-DL-tryptophan, and human albumin. Improving the viability of an organ damaged by ischemia and/or reperfusion may encompass preserving mitochondrial function or decreasing oxidative damage. Other measures known in the art for evaluating the viability of an organ may also be used, including but not limited to measures of cellular function (e.g., metabolic capacity, ATP content, etc.), measures of cellular damage (e.g. histological assessment, morphological changes, etc.), measures of inflammation, and/or measures of the organ's function.

In one embodiment, the disclosure encompasses methods for preserving mitochondrial function in an organ with ischemia-reperfusion damage. Mitochondrial function, as used herein, may be measured by respiratory control ratio (RCR), which is an indicator of the coupling state of mitochondria. Generally speaking, RCR represents the ratio of the oxidation rate in the presence of excess substrate and adenosine diphosphate (State 3) to the oxidation rate after ADP has been phosphorylated to a steady state concentration (State 4). In some embodiments, mitochondrial function is significantly preserved in an organ with ischemia-reperfusion damage by administering a composition comprising 20 ppm or less of $NO_x$ gas directly to the organ. As used herein, "significantly preserved" refers to less than 5%, 10%, 15%, 20%, 25%, 30%, 35%, 40%, 45%, 50%, 55%, 60%, 65%, 70%, 75%, 80%, 85%, 90% or less than 95% difference in mitochondrial function between an organ treated with $NO_x$ gas as described herein, and a control organ that has not undergone ischemia-reperfusion. Stated another way, significantly preserved may refer to an improvement in mitochondrial function compared to a similar organ that has undergone similar ischemia-reperfusion damage but has not been administered direct, continuous $NO_x$ gas. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In other embodiments, the disclosure encompasses methods for decreasing oxidative damage to an organ with ischemia-reperfusion damage. Generally speaking, the method comprises continuously administering a composition comprising 20 ppm or less of $NO_x$ gas directly to the organ. As used herein, "decreased oxidative damage" or "reduced oxidative damage" may be measured in comparison to an organ treated under similar conditions, but that is not directly and continuously administered $NO_x$ gas. For instance, oxidative damage may be decreased by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. In a specific embodiment, a mitochondrial reactive oxygen species (mtROS) is decreased within an organ with ischemia-reperfusion damage that has been administered direct, continuous $NO_x$, compared to a non-treated control. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In some embodiments, the disclosure encompasses a method for increasing superoxide dismutase 2 (SOD2 or manganese-dependent superoxide dismutase (MnSOD)) activity in an organ with ischemia-reperfusion damage. The method comprises continuously administering a composition comprising 20 ppm or less of $NO_x$ gas directly to the organ, wherein MnSOD activity is increased in the organ compared to a control organ that has not been contacted with a composition of the disclosure. For instance, MnSOD activity may be increased by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. Methods of measuring MnSOD activity are known in the art. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In other embodiments, the disclosure encompasses a method for inhibiting formation of nitrotyrosine in an organ with ischemia-reperfusion damage. The method comprises continuously administering a composition comprising 20 ppm or less of $NO_x$ gas directly to the organ, wherein formation of nitrotyrosine adduct is inhibited in the organ compared to a control organ that has not been contacted with a composition of the invention. For instance, nitrotyrosine formation may be inhibited by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. Methods of measuring formation of nitrotyrosine adduct are known in the art. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™ optionally comprising sodium caprylate, N-acetyl-DL-tryptophan, and human albumin.

In certain embodiments, the disclosure encompasses a method for preventing inactivation of mitochondrial complex I activity, complex II activity, complex III activity, complex IV activity, or a combination thereof, in an organ with ischemia-reperfusion damage. The method comprises continuously administering a composition comprising 20 ppm or less of $NO_x$ gas directly to the organ, wherein administering 20 ppm or less of $NO_x$ gas prevents inactivation of activity of mitochondrial complex I, complex II, complex III, complex IV, or a combination thereof compared to a control organ. In one embodiment, continuously administering a composition comprising 20 ppm or less of $NO_x$ gas directly to the organ prevents inactivation mitochondrial complex I activity. In another embodiment, continuously administering a composition comprising 20 ppm or less of $NO_x$ gas directly to the organ prevents inactivation of mitochondrial complex II activity. In yet another embodiment, continuously administering a composition comprising 20 ppm or less of $NO_x$ gas directly to the organ prevents inactivation of mitochondrial complex III activity. In another embodiment, continuously administering a composition comprising 20 ppm or less of $NO_x$ gas directly to the organ prevents inactivation of mitochondrial complex IV activity. In a preferred embodiment, continuously administering a composition comprising 20 ppm or less of $NO_x$ gas directly to the organ prevents inactivation of mitochondrial complex I and mitochondrial complex II activity. In another preferred embodiment, continuously administering a composition comprising 20 ppm or less of $NO_x$ gas directly to the organ prevents inactivation of mitochondrial complex II and mitochondrial complex III activity. For instance, inactivation of activity in each of the above embodiments may be inhibited by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. Methods of measuring mitochondrial complex I activity, complex II activity, complex III activity, or complex IV activity are known in the art. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In each of the above embodiments, administration of the composition comprising 20 ppm or less of $NO_x$ gas may be for a time necessary to improve viability of the organ. For instance, in some embodiments, administration may be for 5, 10, 15, 30 or 60 min. In other embodiments, administration may be for 1, 2, 3, 4, 5, 6, 7, 8, 9, 10, 11, 12, or more hours. In embodiments where the organ is intended for transplant, administration of the $NO_x$ gas preferably does not exceed a total of 12 hours. In certain embodiments, administration begins at the same time as the ischemia. In other embodiments, administration begins sometime after the ischemia begins, but preferentially as close in time to the start of the ischemia as possible. In some embodiments, administration begins about 5, 10, 15, 20, 25, or 30 min after the start of ischemia. Administration may also start during reperfusion, or alternatively, continue after reperfusion begins. In some instances, administration may continue for 1, 2, 3, 4, 5, 6, 7, 8, 9, 10, 11, 12, or more than 12 hours after reperfusion has begun.

In further embodiments, the methods described above may comprise an additional step, wherein a composition comprising about 20 ppm to about 40 ppm $NO_x$ gas ("a loading dose") is administered for up to about 1 hour, immediately prior to administration of the composition comprising 20 ppm or less of $NO_x$ gas. For example, the loading dose may be administered for about 10 minutes, about 15 minutes, about 20 minutes, about 30 minutes, or for about 10 minutes to about 30 minutes. In another example, the loading dose may be administered for about 30 minutes, about 35 minutes, about 40 minutes, about 40 minutes, about 45 minutes, about 50 minutes, about 55 minutes, about 60 minutes, or for 30 minutes to 60 minutes. With the exception of the nitric oxide concentration, the two compositions may be the same. Alternatively, the two compositions may be different. The concentration of nitric oxide in the loading dose may be decreased in increments over the period of time that is up to about one hour until the nitric oxide concentration is 20 ppm or lower. The rate of decrease may or may not be constant. Alternatively, the concentration of nitric oxide in the loading dose may be held constant over the period of time that is up to about one hour, and then decreased to a nitric oxide concentration of 20 ppm or less. In preferred embodiments, the two compositions are the same, and the compositions are a perfusion fluid, preferably an acellular perfusion fluid. In further embodiments, the acellular perfusion solution is Steen Solution™, optionally comprising sodium caprylate, N-acetyl-DL-tryptophan, and human albumin. In exemplary embodiments, the organ is a heart, a lung, or a kidney.

(c) Methods to Improve the Viability of an Organ Intended for Transplant

An organ with ischemia-reperfusion damage encompasses an organ intended for transplant. Hence, the present disclosure encompasses methods for improving the viability of an organ intended for transplant. Such methods comprise continuously administering a composition comprising $NO_x$ gas directly to an organ via an organ perfusion system or ventilation for up to 12 hours. Stated another way, the organ will be in direct contact with the $NO_x$ gas, without interruption, from the time of organ procurement up until grafting in the recipient. Procurement, as used herein, refers to both the identification of the organ donor, as well as to organ removal, and can be used interchangeably with either term. In some embodiments, the composition is administered after the organ has been harvested from a donor. In other embodiments, the composition is administered while the organ is within a donor. In these embodiments, a donor may be a brain dead donor or a non-heart beating donor. In some examples, administration may be for 5, 10, 15, 30 or 60 min. In other examples, administration may be for 1, 2, 3, 4, 5, 6, 7, 8, 9, 10, 11, or 12 hours. Suitable compositions comprising $NO_x$ gas are described in Section (a). In preferred embodiments, the composition is a perfusion fluid, even more preferably an acellular perfusion fluid. In further embodiments, the acellular perfusion solution is Steen Solution™, optionally comprising sodium caprylate, N-acetyl-DL-tryptophan, and human albumin. Without wishing to be bound by theory, it is believed that methods of the present disclosure may increase the number of organs available for transplant by improving the viability of organs that would not have previously satisfied the criteria for transplant, such that more organs can be used from more donors (e.g., marginal brain dead donors, non-heart beating donors, etc.). Improving the viability of an organ intended for transplant may encompass, in part, preserving mitochondrial function or decreasing oxidative damage in the organ. Other measures known in the art for evaluating the viability of an organ may also be used, including but not limited to measures of cellular function (e.g., metabolic capacity, ATP content, etc.), measures of cellular damage (e.g. histological assessment, morphological changes, etc.), measures of inflammation, and/or measures of the organ's function. In exemplary embodiments, the organ is a heart, a lung, or a kidney.

In one embodiment, the disclosure encompasses methods for preserving mitochondrial function in an organ intended for transplant. Mitochondrial function, as used herein, may be measured by respiratory control ratio (RCR), which is an indicator of the coupling state of mitochondria. Generally speaking, RCR represents the ratio of the oxidation rate in the presence of excess substrate and adenosine diphosphate (State 3) to the oxidation rate after ADP has been phosphorylated to a steady state concentration (State 4). In some embodiments, mitochondrial function is significantly preserved in an organ intended for transplant by administering a composition comprising 20 ppm or less of $NO_x$ gas directly to the organ. As used herein, "significantly preserved" refers to less than 5%, 10%, 15%, 20%, 25%, 30%, 35%, 40%, 45%, 50%, 55%, 60%, 65%, 70%, 75%, 80%, 85%, 90% or less than 95% difference in mitochondrial function between an organ treated with $NO_x$ gas as described herein, and a control organ that has not been treated with $NO_x$ gas. Stated another way, significantly preserved may refer to an improvement in mitochondrial function compared to a similar organ intended for transplant that has undergone similar ischemia-reperfusion damage but has not been administered direct, continuous $NO_x$ gas. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In a particular embodiment, the disclosure encompasses a method for decreasing oxidative damage to an organ intended for transplant. For instance, a mitochondrial reactive oxygen species (mtROS) may be decreased within an organ intended for transplant. Such a method comprises continuously administering a composition comprising 20 ppm or less of $NO_x$ gas directly to the organ. The direct, continuous administration may occur before the organ is removed from the donor, during transport/storage, during transplant into the recipient, post-transplant into the recipient, or any combination thereof. In preferred embodiments, the organ will be in direct contact with the $NO_x$ gas, without interruption, from the time of organ removal up until grafting in the recipient. As used herein, "decreased oxidative damage" or "reduced oxidative damage" may be measured in comparison to an organ treated under similar conditions, but that is not directly and continuously administered $NO_x$ gas. For instance, oxidative damage may be decreased by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. In a specific embodiment, a mitochondrial reactive oxygen species (mtROS) is decreased within an organ with ischemia-reperfusion damage that has been administered direct, continuous $NO_x$, compared to a non-treated control. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In some embodiments, the disclosure encompasses a method for increasing superoxide dismutase 2 (SOD2 or manganese-dependent superoxide dismutase (MnSOD)) activity in an organ intended for transplant. The method comprises continuously administering a composition comprising 20 ppm or less of $NO_x$ gas directly to the organ, wherein MnSOD activity is increased in the organ compared to a control organ that has not been contacted with a composition of the disclosure. For instance, MnSOD activity may be increased by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. The direct, continuous administration may occur before the organ is removed from the donor, during transport/storage, during transplant into the recipient, post-transplant into the recipient, or any combination thereof. In preferred embodiments, the organ will be in direct contact with the $NO_x$ gas, without interruption, from the time of organ removal up until grafting in the recipient. Methods of measuring MnSOD activity are known in the art. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In other embodiments, the disclosure encompasses a method for inhibiting formation of nitrotyrosine in an organ intended for transplant. The method comprises continuously administering a composition comprising 20 ppm or less of $NO_x$ gas directly to the organ, wherein formation of nitrotyrosine adduct is inhibited in the organ compared to a control organ that has not been contacted with a composition of the disclosure. For instance, nitrotyrosine formation may be inhibited by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. The direct, continuous administration may occur before the organ is removed from the donor, during transport/storage, during transplant into the recipient, post-transplant into the recipient, or any combination thereof. In preferred embodiments, the organ will be in direct contact with the $NO_x$ gas, without interruption, from the time of organ removal up until grafting in the recipient. Methods of measuring formation of nitrotyrosine adduct are known in the art. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In certain embodiments, the disclosure encompasses a method for preventing inactivation of mitochondrial complex I activity, complex II activity, complex III activity, complex IV activity, or a combination thereof, in an organ intended for transplant. The method comprises continuously administering a composition comprising 20 ppm or less of $NO_x$ gas directly to the organ, wherein administering 20 ppm or less of $NO_x$ gas prevents inactivation of activity of mitochondrial complex I, complex II, complex III, complex IV, or a combination thereof compared to a control organ. In one embodiment, continuously administering a composition comprising 20 ppm or less of $NO_x$ gas directly to the organ prevents inactivation mitochondrial complex I activity. In another embodiment, continuously administering a composition comprising 20 ppm or less of $NO_x$ gas directly to the organ prevents inactivation of mitochondrial complex II activity. In yet another embodiment, continuously administering a composition comprising 20 ppm or less of $NO_x$ gas directly to the organ prevents inactivation of mitochondrial complex III activity. In another embodiment, continuously administering a composition comprising 20 ppm or less of $NO_x$ gas directly to the organ prevents inactivation of mitochondrial complex IV activity. In a preferred embodiment, continuously administering a composition comprising 20 ppm or less of $NO_x$ gas directly to the organ prevents inactivation of mitochondrial complex I and mitochondrial complex II activity. In another preferred embodiment, continuously administering a composition comprising 20 ppm or less of $NO_x$ gas directly to the organ prevents inactivation of mitochondrial complex II and mitochondrial complex III activity. For instance, inactivation of activity in each of the above embodiments may be inhibited by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. The direct, continuous administration may occur before the organ is removed from the donor, during transport/storage, during transplant into the recipient, post-transplant into the recipient, or any combination thereof. In preferred embodiments, the organ will be in direct contact with the $NO_x$ gas, without interruption, from the time of organ removal up until grafting in the recipient. Methods of measuring mitochondrial complex I activity, complex II activity, complex III activity, or complex IV activity are known in the art. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In each of the methods above, administration of a composition comprising $NO_x$ gas directly to the organ via an organ perfusion system may occur via an organ perfusion system, a ventilator, or any combination thereof, for 1, 2, 3, 4, 5, 6, 7, 8, 9, 10, 11, or 12 hours. In embodiments where an organ perfusion system and a ventilator are used in combination, an organ perfusion system and a ventilator may be used simultaneously to administer a composition comprising $NO_x$ gas directly to the organ. Alternatively, or in addition, an organ perfusion system and a ventilator may be used sequentially to administer a composition comprising $NO_x$ gas directly to the organ, including various amounts of overlap between the two methods of administration (e.g. no overlap, or an overlap of a few seconds, minutes, or hours). For example, administration may occur first with a ventilator and then a perfusion system, or vice versa.

In further embodiments, the methods described above may comprise an additional step, wherein a composition comprising about 20 ppm to about 40 ppm $NO_x$ gas ("a loading dose") is administered for up to about 1 hour, immediately prior to administration of the composition comprising 20 ppm or less of $NO_x$ gas, wherein administration of the $NO_x$ gas does not exceed a total of 12 hours. For example, the loading dose may be administered for about 10 minutes, about 15 minutes, about 20 minutes, about 30 minutes, or for about 10 minutes to about 30 minutes, and the composition comprising 20 ppm or less of $NO_x$ gas would then be administered for about 11.8 hours or less. In another example, the loading dose may be administered for about 30 minutes, about 35 minutes, about 40 minutes, about 40 minutes, about 45 minutes, about 50 minutes, about 55 minutes, about 60 minutes, or for 30 minutes to 60 minutes, and the composition comprising 20 ppm or less of $NO_x$ gas would then be administered for 11.5 hours or less. With the exception of the nitric oxide concentration, the two compositions may be the same. Alternatively, the two compositions may be different. The concentration of nitric oxide in the loading dose may be decreased in increments over the period of time that is up to about one hour until the nitric oxide concentration is 20 ppm or lower. The rate of decrease may or may not be constant. Alternatively, the concentration of nitric oxide in the loading dose may be held constant over the period of time that is up to about one hour, and then decreased to a nitric oxide concentration of 20 ppm or less. In preferred embodiments, the two compositions are the same, and the compositions are a perfusion fluid, preferably an acellular perfusion fluid. In further embodiments, the acellular perfusion solution is Steen Solution™, optionally comprising sodium caprylate, N-acetyl-DL-tryptophan, and human albumin. In exemplary embodiments, the organ is a heart, a lung, or a kidney.

(d) Methods to Improve the Post-Transplant Performance of an Organ Intended for Transplantation Another aspect of the disclosure encompasses methods to improve the post-transplant performance of an organ intended for transplantation. The method comprises continuously administering a composition comprising 20 ppm or less of $NO_x$ gas directly to the organ via an organ perfusion system for up to 12 hours. In some examples, administration may be for 5, 10, 15, 30 or 60 min. In other examples, administration may be for 1, 2, 3, 4, 5, 6, 7, 8, 9, 10, 11, or 12 hours. Suitable compositions comprising $NO_x$ gas are described in Section (a). In preferred embodiments, the composition is a perfusion fluid, even more preferably an acellular perfusion fluid. Improving the post-transplant performance of an organ intended for transplantation may encompass preserving mitochondrial function or decreasing oxidative damage. Other measures known in the art for evaluating the viability of an organ may also be used, including but not limited to measures of cellular function (e.g., metabolic capacity, ATP content, etc.), measures of cellular damage (e.g. histological assessment, morphological changes, etc.), measures of inflammation, and/or measures of the organ's function. In exemplary embodiments, the organ is a heart, a lung, or a kidney.

In one embodiment, the disclosure encompasses methods for preserving mitochondrial function in a post-transplanted organ. Mitochondrial function, as used herein, may be measured by respiratory control ratio (RCR), which is an indicator of the coupling state of mitochondria. Generally speaking, RCR represents the ratio of the oxidation rate in the presence of excess substrate and adenosine diphosphate (State 3) to the oxidation rate after ADP has been phosphorylated to a steady state concentration (State 4). In some embodiments, mitochondrial function is significantly preserved in an organ post-transplantation by administering a composition comprising 20 ppm or less of $NO_x$ gas directly to the organ. As used herein, "significantly preserved" refers to less than 5%, 10%, 15%, 20%, 25%, 30%, 35%, 40%, 45%, 50%, 55%, 60%, 65%, 70%, 75%, 80%, 85%, 90% or less than 95% difference in mitochondrial function between an organ treated with $NO_x$ gas as described herein, and a control organ that has not been directly, continuously, treated with $NO_x$ gas. Stated another way, significantly preserved may refer to an improvement in mitochondrial function compared to a similar organ that has undergone similar ischemia-reperfusion damage but has not been administered direct, continuous $NO_x$ gas. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In other embodiments, the disclosure encompasses methods for decreasing oxidative damage in a post-transplanted organ. Generally speaking, the method comprises continuously administering a composition comprising 20 ppm or less of $NO_x$ gas directly to the organ. As used herein, "decreased oxidative damage" or "reduced oxidative damage" may be measured in comparison to an organ treated under similar conditions, but that is not directly and continuously administered $NO_x$ gas. For instance, oxidative damage may be decreased by 5%, 10%, 15%, 20%, 25%, 30%, 35%, 40%, 45%, 50%, 55%, 60%, 65%, 70%, 75%, 80%, 85%, 90% or 95% in comparison to an organ treated under similar conditions, but that is not directly and continuously administered $NO_x$ gas. In a specific embodiment, a mitochondrial reactive oxygen species (mtROS) is decreased within an organ post-transplant that has been administered direct, continuous $NO_x$, compared to a non-treated control. Suitable compositions comprising $NO_x$ gas are described in Section (a). In preferred embodiments, the composition is a perfusion fluid, even more preferably an acellular perfusion fluid, and the organ is a heart, a lung, or a kidney. In further embodiments, the acellular perfusion solution is Steen Solution™, optionally comprising sodium caprylate, N-acetyl-DL-tryptophan, and human albumin.

In further embodiments, the methods described above may comprise an additional step, wherein a composition comprising about 20 ppm to about 40 ppm $NO_x$ gas ("a loading dose") is administered for up to about 1 hour, immediately prior to administration of the composition comprising 20 ppm or less of $NO_x$ gas, wherein administration of the $NO_x$ gas does not exceed a total of 12 hours. For example, the loading dose may be administered for about 10 minutes, about 15 minutes, about 20 minutes, about 30 minutes, or for about 10 minutes to about 30 minutes, and the composition comprising 20 ppm or less of $NO_x$ gas would then be administered for about 11.8 hours or less. In another example, the loading dose may be administered for about 30 minutes, about 35 minutes, about 40 minutes, about 40 minutes, about 45 minutes, about 50 minutes, about 55 minutes, about 60 minutes, or for 30 minutes to 60 minutes, and the composition comprising 20 ppm or less of $NO_x$ gas would then be administered for 11.5 hours or less. With the exception of the nitric oxide concentration, the two compositions may be the same. Alternatively, the two compositions may be different. The concentration of nitric oxide in the loading dose may be decreased in increments over the period of time that is up to about one hour until the nitric oxide concentration is 20 ppm or lower. The rate of decrease may or may not be constant. Alternatively, the concentration of nitric oxide in the loading dose may be held constant over the period of time that is up to about one hour, and then decreased to a nitric oxide concentration of 20 ppm or less. In preferred embodiments, the two compositions are the same, and the compositions are a perfusion fluid, preferably an acellular perfusion fluid. In exemplary embodiments, the organ is a heart, a lung, or a kidney. In further embodiments, the acellular perfusion solution is Steen Solution™ optionally comprising sodium caprylate, N-acetyl-DL-tryptophan, and human albumin.

(e) Methods for Transplantation

In another aspect, the present disclosure provides methods for transplantation. The method comprises (a) continuously administering a composition comprising 20 ppm or less of $NO_x$ gas directly to an organ intended for transplant for up to 12 hours, and (b) transplanting the organ into a recipient. Administration may be for 5, 10, 15, 30 or 60 minutes. Alternatively, administration may be for 1, 2, 3, 4, 5, 6, 7, 8, 9, 10, 11, or 12 hours. In some embodiments, the composition comprises 1 ppm to 20 ppm nitric oxide. In other embodiments, the composition comprises about 1 ppm to about 10 ppm nitric oxide, about 5 ppm to about 15 ppm nitric oxide, or about 10 ppm to 20 ppm. In other embodiments, the composition comprises about 1 ppm, about 2 ppm, about 3 ppm, about 4 ppm, about 5 ppm, about 6 ppm, about 7 ppm, about 8 ppm, about 9 ppm, about 10 ppm, about 11 ppm, about 12 ppm, about 13 ppm, about 14 ppm, about 15 ppm, about 16 ppm, about 17 ppm, about 18 ppm, about 19 ppm, or about 20 ppm nitric oxide. Suitable compositions comprising $NO_x$ gas are described in Section (a). In preferred embodiments, the composition is a perfusion fluid, even more preferably an acellular perfusion fluid. In further embodiments, the acellular perfusion solution is Steen Solution™, optionally comprising sodium caprylate, N-acetyl-DL-tryptophan, and human albumin. In exemplary embodiments, the organ is a heart, a lung, or a kidney.

In certain embodiments, the organ intended for transplant has been removed from a donor prior to step (a) above. In these embodiments, administration begins sometime after the ischemia begins, but preferentially as close in time to the start of the ischemia as possible. For example, administration may begin about 5, 10, 15, 20, 25, or 30 min after the start of ischemia. The timing of administration may or may not correspond to the start of reperfusion.

In further embodiments, the method may comprise an additional step, wherein a composition comprising about 20 ppm to about 40 ppm $NO_x$ gas ("a loading dose") is administered for up to about 1 hour ("a loading period"), immediately prior to administration of the composition comprising 20 ppm or less of $NO_x$ gas. For example, the loading dose may be administered for about 10 minutes, about 15 minutes, about 20 minutes, about 30 minutes, or for about 10 minutes to about 30 minutes. In another example, the loading dose may be administered for about 30 minutes, about 35 minutes, about 40 minutes, about 40 minutes, about 45 minutes, about 50 minutes, about 55 minutes, about 60 minutes, or for 30 minutes to 60 minutes. With the exception of the nitric oxide concentration, the two compositions may be the same. Alternatively, the two compositions may be different. The concentration of nitric oxide in the loading dose may be decreased in increments over the loading period until the nitric oxide concentration is 20 ppm or lower. The rate of decrease may or may not be constant. Alternatively, the concentration of nitric oxide in the loading dose may be held constant over the loading period, and then decreased to a nitric oxide concentration of 20 ppm or less. In preferred embodiments, the two compositions are the same, and the compositions are a perfusion fluid, preferably an acellular perfusion fluid. In further embodiments, the acellular perfusion solution is Steen Solution™ optionally comprising sodium caprylate, N-acetyl-DL-tryptophan, and human albumin. In exemplary embodiments, the organ is a heart, a lung, or a kidney.

EXAMPLES

The following examples illustrate various iterations of the invention.

Example 1: Lung Transplant Protocol

The study includes twenty lungs in total (8 lungs with gNO and perfusate, 8 lungs with perfusate alone, and 4 lungs with ventilated gNO and perfusate) as per modified standard lung donor inclusion criteria. The 3-arm study includes gNO added to the perfusate, perfusate alone, and ventilated gNO and perfusate (pilot study). A XVivo perfusion device system with acellular perfusate (Steen solution) will be used. The maximum cold ischemic time for the lungs will be 8-10 hours. The Duration of Ex-Vivo Lung Perfusion will be up to 12 hours. The health of the lungs is assessed by a grading system, biomarker assessment, and histopathological assessment.

Grading System

The grading System includes a 0-10 grade (aggregate score) using a composite measure of 3 variables. The three variables are 1) Delta $PaO_2$ weighted as 0-4 using 4 categories: 0=<350 mmHg; 1=≥350-<400 Hg; 2=≥400-<450 mm Hg; 3=≥450-<500 mmHg; 4=≥500 mmHg, 2) Static compliance of the lungs weighted as 0-4 (change from baseline): 0=no improvement or worsening in compliance; 1=1-3% improvement; 2=4-7% improvement; 3=8-11% improvement and 4=12-15% improvement in compliance, and 3) Pulmonary vascular resistance (PVR) weighted as 0-2: 0=no change in PVR or increase in PVR; 1=1-7% decrease in PVR; 2=8-15% decrease in PVR.

Biomarker Assessment

Damage Assessment Molecular Proteins (DAMPs), High Mobility Group box-1 (HMGB1), S100A8 (MRP8, calgranulin A), S100A9 (MRP14, calgranulin B), and Serum amyloid A (SAA) will be the biomarkers assessed. The cytokines of interest are TNF alpha-1, IL1-beta, IL-6, NLRP3, IL-10 and Donor Cell Free DNA.

Histopathological Assessment

The histopathological parameters to be assessed are interstitial and intra-alveolar edema, hyaline membrane formation, and evidence of vascular integrity/injury (CD31 staining).

Donor Lung Procurement

Current clinical practice after organ retrieval from the donor is for cold static preservation till it is transplanted to a recipient. During retrieval, lungs undergo a cold pulmonary flush using low potassium dextran preservation solution which is coupled with topical cooling and lung ventilation. Lungs are then transported at 4-C in a static inflated state. Hypothermia reduces metabolic activity with maintenance of cell viability, essentially slowing down cell death processes, in the face of ischemia (5% of metabolic rate at 37 degrees centigrade). Cold temperature preservation is therefore the mainstay of prior art lung preservation. However, there is significant decrease in organ metabolic functions, which precludes the possibility of meaningful lung evaluation and recovery.

The Donor lung procurement technique of this study will be as follows. Perform bronchoscopy and median sternotomy. Open the pericardium and plural spaces. Recruit both lungs and evaluate $PO_2$ on 100% $FiO_2$ challenge. Heparinize systemically. Place pursestring sutures on the main pulmonary aorta (PA). Cannulate the PA through pursestring. De-air cannula and connect to de-aired Perfadex tubing (The Perfadex bag should only drain via gravity (non-pressurized), and the bag should not be greater than 1 meter higher than the lungs). Administer 500 mcg Alprostidil directly into the main PA. Ligate the Superior Vena Cava (SVC), vent left and right atrium, and cross clamp aorta.

Deliver 4 liters of Perfadex antegrade. Ensure brisk and rapid drainage of effluent in both right and left atrium. Place topical ice on both lungs (however, only one lung to be used per cycle). Maintain ventilation with room air $FiO_2$ at 4-6 ml/kg/min tidal volume and a rate of 10 breaths per minute. Once infusion is complete, excise heart. If the heart is being transplanted, incise PA at the PA bifurcation. Do not divide branch PAs. If the heart is not being transplanted, incise PA at the RVOT just proximal to the pulmonic valve. Ensure that the left atrial cuff remains intact. Infuse pulmonary veins retrograde with cold Perfadex (total 2 liters). Incise pericardium at the level of the diaphragm bilaterally and carry across to completely separate pericardium from diaphragm. Incise inferior pulmonary ligament bilaterally. Dissect posterior pericardium from posterior mediastinum cephalad until carina. Dissect trachea cephalad until the level of the cricoid cartilage. Retract endotracheal tube to the level of the larynx. Inflate lungs to 50% total lung capacity at 50% $FiO_2$. Divide trachea above cricoid cartilage with 2 staple loads. Dissect posterior trachea from posterior mediastinum (esophagus) caudal towards the diaphragm. Dissect left PA from aortic arch, divide the ligementum arteriosum. Remove lungs and store in iced Perfadex solution. If the heart has been procured for transplant, excise 10 cm of donor descending aorta and place in same cold Perfadex solution bag as the lungs. This will be used later for reconstruction of the pulmonary artery.

Ex-Vivo Lung Perfusion (EVLP)

The main principle of EVLP consists of perfusing and ventilating the lungs external to the body in a closed container that maintains the temperature, moisture and sterility of the donor organ. The EVLP circuit consists of a centrifugal pump that circulates the perfusate while passing through a membrane gas exchanger and a leukocyte depletion filter before entering the pulmonary artery (PA). This system is fairly similar to that used for cardiac surgery extra-corporeal circuit (ECC). Acellular Steen's solution will be used as the perfusate for the EVLP process.

Briefly the EVLP process is as follows. Lungs are placed in a special covered plastic chamber to fix the lungs in a stable position during ventilation and provide a warm and humid environment. The perfusate solution (propelled by the centrifugal pump) enters the lung through a cannula positioned in the pulmonary artery (PA). The return flow from the lung is passive through the pulmonary veins (PV), by gravity, and the perfusion solution is collected in a reservoir before it gets recirculated through the pump and the membrane oxygenator. The gas oxygenator is connected to a tank with a special gas mixture of oxygen (6%), carbon dioxide (8%) and nitrogen (86%). The ventilator provides airway to the lungs and is connected to a tracheal chest tube.

Lung grafts (cooled during organ harvest and undergoes static cold preservation) are gradually rewarmed over a period of 45 minutes. The lung perfusion is started a low flow rate (0.10-0.15 l/min) and then gradually increased in parallel with the rewarming, to a delivery in the pulmonary artery of 40-50% of an estimated cardiac output (at 70 ml/kg/min). The PA pressure needs to be kept low (<15-20 mmHg) as the capillary-alveolar barrier has been weakened by the ischemia-reperfusion injury (IRI) following the organ procurement, as the IRI has damaged the integrity, increases the permeability of the alveolar capillary membrane and can lead to the formation of pulmonary edema.

During the rewarming phase, $O_2$ supply to the graft is delivered by the membrane oxygenator, which then delivers a $pCO_2$ and pH close to the usual measurement in PA. Catheters are placed in situ which continuously measure PA and left atrial (LA) pressure through EVLP process. Mechanical ventilation of the lungs is initiated when the temperature of the perfusate reached 32 degrees centigrade (usually about 30 mins after start of perfusion).

The following is the 19 Step Progression of an EVLP process. This is a quick reference guide, not an exhaustive protocol.

Step 1. Transportations of lungs to XPS. Comply with UNOS standards.

Step 2. Cannulation of lungs. LA cannula (green) trimmed to approximate atrial opening, and sutured in with a running polypropylene suture. PA cannula (yellow), open the PA lumen and insert the XVIVO cannula. If the pulmonary artery requires reconstruction, sew a segment of donor descending aorta to the pulmonary artery and then cannulate as above. Using either umbilical tape or silk tie, secure the cannula in place across the grove, back tie onto cannula underneath pressure line. Intubation, clamp the trachea to prevent deflation. Insert ET tube into trachea, and secure in place with either umbilical tape or silk tie.

Step 3. Back table flush. Retrograde flush one liter cold Perfadex, check for leaks around cannulation. Keep ET tube clamped Step 4. System set up. Set up perfusion circuit on the XPS with PGM's. Open dome by removing plastic, then 1st layer of blue wrapping on a back table. Place clear U drape on the top bar of the XPS that's over the blue table & secure w/clips on the XPS covering the blue table, leaving the "U" opening of the U drape on the right side, so the tubing can pass through. Open 2nd blue layer of dome on the blue table of Xvivo machine in a sterile manner. Attach the red ⅜ inch drain line to back of dome & pass the 4 line around the outside of the pole & into red roller pump. Hand off drain bag & attach orange & red lines to bag. Add return line from the top of the reservoir, to the stopcock. Turn stopcock on red line off to reservoir & open to drain bag. Set transducers and flush with sterile saline, add blue tubing for the heater/cooler, and then the venous gas line to the back of the Quadrox. Check to ensure you have sufficient amount of O2 and tri gas.

Step 5. System purge. Add 1500 ml of STEEN to reservoir, add drugs (Heparin 10,000 units, Methylprednisolone 500 mg, Ceftazidine 1 gm), turn on Cardiohelp and heater cooler (set at 23) first, and then the UPS followed by touch screen, and ventilator. Purge the perfusion circuit, by removing the yellow cap on the back of the Quadrox, any clear cap on the reservoir, and the blue cap on the leukocyte filter. Increase the Cardiohelp to 1000 RPM's and checks the circuit for leaks, after one-minute increase Cardiohelp to 3000 RPM's. After a few minutes, increase Cardiohelp to 5000 RPM's and let it run for one minute, check to make sure all the air is out of the line, and decrease RPM's below 250.

Step 6. Data set up logging. In the set up page of the touch screen fill in the required information, and change PH to an acceptable level to alarm (6.8). On the service page hit the green PGM calibration button, and fill in the PH and $PO_2$ based of the calibration numbers that is found on PGM packaging. On the main screen set the timers (count up for 1 & 2 and count down for #3, (set #3 for 10 minutes)). On the ventilator press setup, Mode (S) CMV+ press confirm. Put in parameters from spreadsheet press confirm. Set alarms also per parameters on flow sheet. At the I/O panel on the back side of the XPS place the Inhale port on right & exhale port (blue tip) on left of the lung circuit. Connect flow sensor tubing, clear on white, and blue on blue. Connect venous gas mix line. Connect high pressure $O_2$ line. Humidifying filter goes on the lung-end of circuit between flow sensor & ET-T. Do Pre-op check, press system, press test & calibrate. Select each calibration test one at a time. Press tightness & follow steps, press flow sensor & follow steps, $O_2$ cell & does not require a test.

Step 7. Retrograde flush. Using sterile tubing clamps redirect the flow in the perfusion circuit so the flow goes in the LA, and out the PA. Starting at 750 RPM's, slowly increase RPM's until you have sufficient flow to fill the PA cannula, and flush out lung until the STEEN solution is clear of blood, should be about 250 cc. Direct this STEEN solution into the dump bag with the recycle pump. Once clear of blood, attach cannula and circuit on the LA side making sure the lung is full of STEEN solution. There should be enough STEEN to go through the LA cannula and fill the PA cannula, then reset the direction of the recycle pump to go in the reservoir. Re-position the sterile clamps to top of the PA cannula and attach to circuit. Clamp Bridge (should be the only clamp).

Step 8. Calibration. Calibrate perfusion flow sensor, and the pressure sensors. (Flow sensor can be done before lungs are placed on circuit for retrograde). Pressure sensors should be done right after retrograde and the lungs are on circuit, (Top of fluid level—where cannulas meet lungs as well as pressure stopcocks, should all be at same level, with a syringe pull from the pressure sensor line, to fill with STEEN, make sure to move the stopcock to shut off from saline).

Step 9. Antegrade. Start timer one (perfusion timer), follow the EVLP workup sheet for the first hour settings.

Step 10. 1st hour step up. Every 10 min there will be a change made to the Cardiohelp, and the heater cooler until the max for each has been reached. Ventilation cannot start until temperature reaches 32° C. At 32° C. a bronch may be done. The tri-gas sweep needs to start at the same time the ventilator starts.

Step 11. Lung recruitment. Not to be confused with the $O_2$ challenge, lung recruitment is a manual hold of the expiratory key on the ventilator for 15 sec. this key should be hit after inspiration, to hold expiration.

Step 12. $O_2$ challenge. $O_2$ challenge will involve changing the settings on the ventilator only, follow the recruitment settings on the EVLP workup sheet. (Multiply IBW×10 for Vt, increase $FiO_2$ to 100%, BPM up to 10)

Step 13. Gas draw. Arterial and venous perfusate samples should be drawn from the transducer, in the last minute of the $O_2$ challenge. Hit the gray PH button on the main screen, to lock in the gas value. (Do a pin point calibration on both LA, and PA for the PH, when results return from the lab.) Record appropriate information, then reset to normal settings on the ventilator (leave the Alarm and settings high at this point).

Step 14. X-ray. After the $O_2$ challenge has been completed, an x-ray should be performed to have a baseline comparison for future x-ray.

Step 15. Steen dilution. After recruitment, challenge, gas draw, and x-ray have been completed (or during X-ray), dilution of STEEN will be needed. Open on the touch screen the +/− pump control window. Touch the "remove" button and slide your finger down until the remove button is locked on (if clamp method is being used, remove clamp instead). Watch the level drop in the reservoir. Once you have removed enough STEEN, touch the "remove" button to shut it off (replace clamp, if clamp method is being used). Add 3 or 4 bottles of fresh STEEN. Another dose of medications can also be added.

Step 16. Maintain and evaluate lungs for the next 3-5 hours. Repeat steps 12, and 13 (minus pin point calibration), at the 50 min mark of each hour Step 17. Repeat step 14 about one hour before removing lungs for transplant. Comparing the first x-ray and the second x-ray will help in determining if the lungs are transplantable.

Step 18. Repeat step 15 after 6 hours of perfusion.

Step 19. Rapid cool down. After the lungs have been accepted to transplant, set the heater/cooler to 15° C., at 32° C. clamp the ET tube when the lungs are 50% inflated, disconnect lungs from the perfusion circuit, and flush with two liters of cold Perfadex, and place in sterile bags with Perfadex. (Similar to standard donor procurement protocol).

Step 20. Clean XPS, and store. Wipe down the surfaces of the XPS with disinfectant, and store with the toggle switch up, and plugged into an outlet for charging. Gas draw should happen at the end of every 10 minute challenge.

Figure 2:
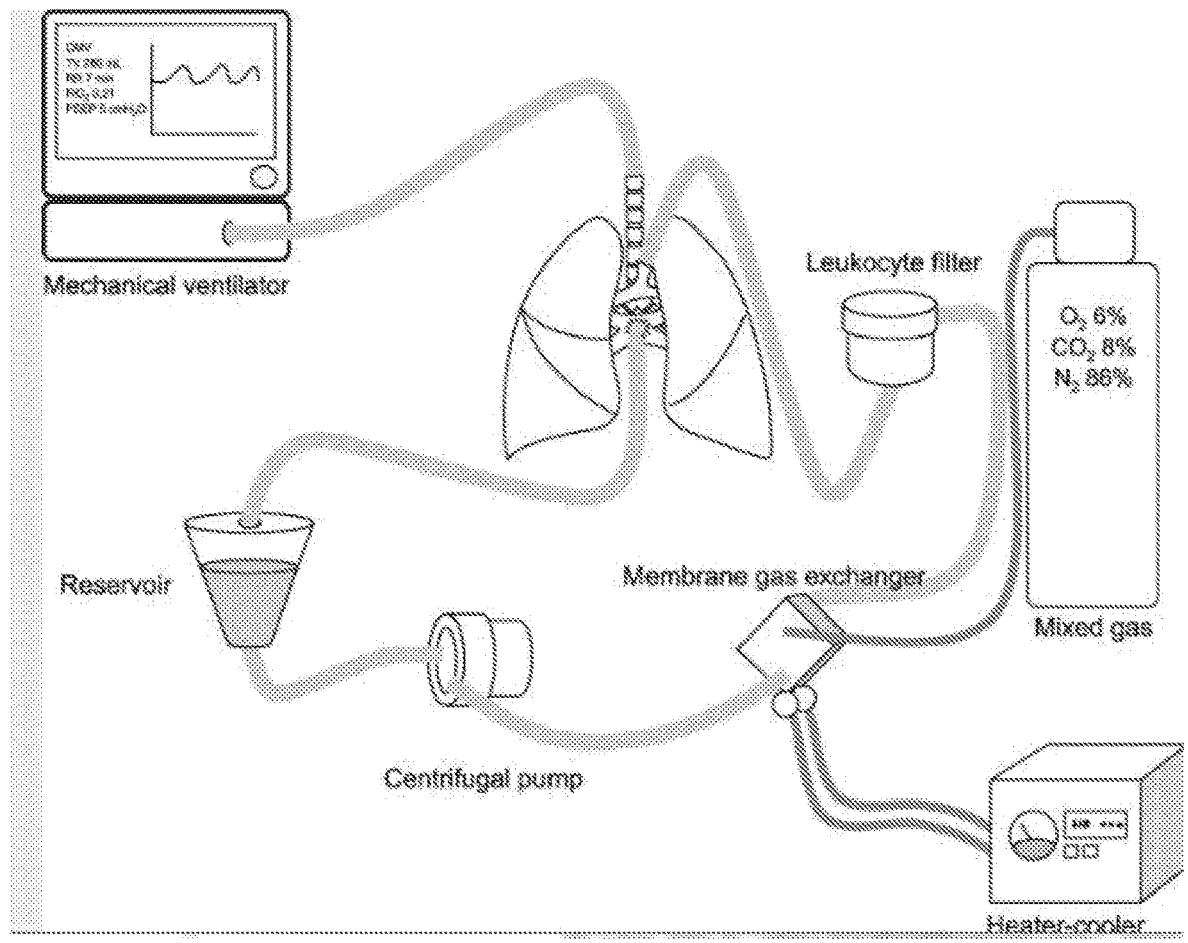
FIG. 2 is an illustration of an embodiment of an EVLP circuit.

See, for reference, FIG. 1 and FIG. 2, which illustrate potential system schematics.

Example 2. Inhaled Nitric Oxide Improves Cerebral Mitochondrial Function in a Blinded, Randomized, Controlled Pediatric Swine Asphyxial Model of Cardiac Arrest Trial Introduction Neurologic injury following pediatric cardiac arrest (CA) remains common. Inhaled nitric oxide (iNO) may mitigate cerebral mitochondrial dysfunction, a critical convergence point for secondary brain injury, triggered by CA. It was hypothesized that following asphyxia and cardiac arrest, animals treated with 20 ppm NO during CPR and four hours post-return of spontaneous circulation (ROSC) will have improved cerebral blood flow (CBF) and improved mitochondrial function as defined by increased respiratory control ratio (RCR) and decreased mitochondrial reactive oxygen species (mtROS) compared with placebo.

Methods 4-week-old swine received 7 minutes of asphyxia, then ventricular fibrillation. Guideline CPR was performed with compression depth (CD)≥⅓ of the chest diameter and standard epinephrine continued for 10 mins or until ROSC, with protocolized post-ROSC care. In a blinded fashion, subjects were randomized (iNO 20 ppm initiated 1 minute into CPR period, n=10, or placebo, n=10). Shams (n=4) did not undergo CA or CPR. Baseline and continuous CBF measurements were taken using invasive clinical and noninvasive optical instrumentation. Cortical and hippocampal tissue were analyzed by high-resolution respirometry to assess mitochondrial function. T-tests and ANOVA were used where applicable. Longitudinal hemodynamic variables were compared using generalized estimating equations to control for within-subject correlation.

Results

7/10 of placebo group and NO 10/10 of NO group (p=0.21) survived. During CPR and post-ROSC there were no significant differences in invasive or noninvasive CBF between treatment groups. Cortex and hippocampal RCR were significantly higher (p=0.04, 0.007), and mtROS generation was significantly lower (p<0.001, p=0.03) in NO treated animals. There were no differences in systemic or pulmonary hemodynamics between NO and placebo groups, but there was a trend toward lower mean pulmonary artery pressure in NO animals during CPR (28.1±9.8 v. 42.6±6.0, p=0.14). NO preserves cerebral mitochondrial function (increased RCR) and limits mtROS production in a porcine model of pediatric CA. Further studies are needed to evaluate this potential neuroprotective effect of NO in ischemia-reperfusion injury and cardiac arrest.

What is claimed is:

1. A method for increasing superoxide dismutase 2 (SOD2 or manganese-dependent superoxide dismutase (MnSOD)) activity in an organ with ischemia-reperfusion damage, the method comprising:
continuously administering a composition comprising 20 ppm or less of NO gas directly to the organ, wherein MnSOD activity is increased in the organ compared to a control organ that has not been contacted with the composition.

2. The method of claim 1, wherein MnSOD activity is increased by 5% to 95% in comparison to an organ treated under similar conditions, but that is not directly and continuously administered NO gas.

3. The method of claim 1, wherein the composition comprises an acellular perfusion fluid.

4. The method of claim 3, wherein the acellular perfusion fluid comprises sodium caprylate, N-acetyl-DL-tryptophan, and human albumin.

5. The method of claim 1, wherein the organ is a heart, a lung, or a kidney.

6. The method of claim 1, wherein administration of the composition is for a time necessary to improve viability of the organ.

7. The method of claim 6, wherein administration of the composition is for 5 to 60 minutes or 1 to 12 hours.

8. The method of claim 1, wherein administration begins at the same time as or within about 5 to 30 minutes after the start of the ischemia.

9. The method of claim 1, wherein administration begins during reperfusion or continues for 1 to 12 hours after reperfusion has begun.

10. A method for inhibiting formation of nitrotyrosine in an organ with ischemia-reperfusion damage, the method comprising:
continuously administering a composition comprising 20 ppm or less of NO gas directly to the organ, wherein formation of nitrotyrosine adduct is inhibited in the organ compared to a control organ that has not been contacted with the composition.

11. The method of claim 10, wherein nitrotyrosine formation is inhibited by 5% to 95% in comparison to an organ treated under similar conditions, but that is not directly and continuously administered NO gas.

12. The method of claim 10, wherein the composition comprises an acellular perfusion fluid.

13. The method of claim 12, wherein the acellular perfusion fluid comprises sodium caprylate, N-acetyl-DL-tryptophan, and human albumin.

14. The method of claim 10, wherein the organ is a heart, a lung, or a kidney.

15. The method of claim 10, wherein administration of the composition is for a time necessary to improve viability of the organ.

16. The method of claim 15, wherein administration of the composition is for 5 to 60 minutes or 1 to 12 hours.

17. The method of claim 10, wherein administration begins at the same time as or within about 5 to 30 minutes after the start of the ischemia.

18. The method of claim 10, wherein administration begins during reperfusion or continues for 1 to 12 hours after reperfusion has begun.

19. A method for preventing inactivation of mitochondrial complex I activity, complex II activity, complex III activity, complex IV activity, or a combination thereof, in an organ with ischemia-reperfusion damage, the method comprising:
continuously administering a composition comprising 20 ppm or less of NO gas directly to the organ, wherein administering 20 ppm or less of NO gas prevents inactivation of activity of mitochondrial complex I, complex II, complex III, complex IV, or a combination thereof compared to a control organ.

20. The method of claim 19, wherein inactivation of activity of mitochondrial complex I, complex II, complex III, complex IV, or a combination thereof is inhibited by 5% to 95% in comparison to an organ treated under similar conditions, but that is not directly and continuously administered NO gas.

21. The method of claim 10, wherein the composition comprises an acellular perfusion fluid.

22. The method of claim 12, wherein the acellular perfusion fluid comprises sodium caprylate, N-acetyl-DL-tryptophan, and human albumin.

23. The method of claim 10, wherein the organ is a heart, a lung, or a kidney.

24. The method of claim 10, wherein administration of the composition is for a time necessary to improve viability of the organ.

25. The method of claim 15, wherein administration of the composition is for 5 to 60 minutes or 1 to 12 hours.

26. The method of claim 10, wherein administration begins at the same time as or within about 5 to 30 minutes after the start of the ischemia.

27. The method of claim 10, wherein administration begins during reperfusion or continues for 1 to 12 hours after reperfusion has begun.

\* \* \* \* \*